United States Patent [19]

Peake

[11] Patent Number: 4,558,163

[45] Date of Patent: Dec. 10, 1985

[54] PROCESS FOR PREPARING 9,10-ANTHRACENEDICARBOXALDEHYDE

[75] Inventor: Steven L. Peake, Ridgefield, Conn.

[73] Assignee: American Cyanamid Company, Stamford, Conn.

[21] Appl. No.: 632,356

[22] Filed: Jul. 19, 1984

[51] Int. Cl.$^4$ ............... C07C 45/33; C07C 47/546
[52] U.S. Cl. ............................................... 568/436
[58] Field of Search ............................. 568/436, 437

[56] References Cited

PUBLICATIONS

Klanderman, Jour. Org. Chem., vol. 31, (1966), 2618–2620.

Primary Examiner—Bernard Helfin
Attorney, Agent, or Firm—Edward A. Conroy, Jr.

[57] ABSTRACT

This disclosure describes a novel process for the preparation of 9,10-anthracenedicarboxaldehyde by the oxidation of 9,10-bis(chloromethyl)anthracene.

5 Claims, No Drawings

PROCESS FOR PREPARING 9,10-ANTHRACENEDICARBOXALDEHYDE

BRIEF SUMMARY OF THE INVENTION

This invention relates to a novel method for the preparation of 9,10-anthracenedicarboxaldehyde by the oxidation of 9,10-bis(chloromethyl)anthracene which may be depicted as follows:

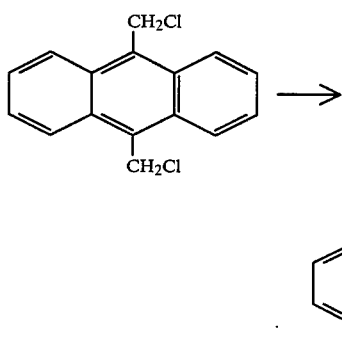

This oxidation is carried out with 2-nitropropane as the oxidizing agent in a binary solvent system consisting essentially of either dimethylsulfoxide or dimethylformamide plus an alkanol having from one to four carbon atoms. The reaction is also carried out in the presence of an alkali metal hydroxide and under an inert atmosphere at temperatures of from about 15° C. to about 85° C. for a period of time of from about one to about six hours.

DETAILED DESCRIPTION OF THE INVENTION

Although 9,10-anthracenedicarboxaldehyde is a valuable synthetic intermediate for the preparation of the cytotoxic agents disclosed in U.S. Pat. No. 4258181; no convenient, simple, and economical procedure for its preparation has heretofore been available. Two methods for the synthesis of 9,10-anthracenedicarboxaldehyde have been reported by G. Rio and B. Sillion, Compt. rend 244, 623 (1957). One method involves a low-yield, multi-step synthesis starting from anthraquinone and is obviously not practical. The other method employs the reaction of 9,10-dibromoanthracene with butyl-lithium to form the 9,10-dilithio derivative which gives 9,10-anthracenedicarboxaldehyde upon treatment with dimethylformamide. This procedure is reasonable but is neither convenient nor economical. Another method was reported by B. H. Klanderman, J. Org. Chem. 31, 2618 (1966) which involves the reaction of 9,10-bis(chloromethyl)anthracene in dimethylsulfoxide with an ethanolic solution of the sodium salt of 2-nitropropane. 9,10-bis-(chloromethyl)anthracene is readily prepared in good yield from anthracene via chloromethylation as reported by M. W. Miller et al, J.A.C.S. 77, 2845 (1955).

A simple, convenient synthesis for 9,10-anthracenedicarboxaldehyde in excellent yields has now been devised which is less hazardous and less polluting than the prior art procedures and which uses inexpensive and easily handled starting materials. This novel process involves the oxidation of 9,10-bis(-chloromethyl)anthracene with 2-nitropropane in a binary solvent system consisting of either dimethylsulfoxide or dimethylformamide and an alkanol having from one to four carbon atoms. Suitable alkanols, of course, are methanol, ethanol, isopropanol, sec.-butanol, etc. The oxidation is carried out in the presence of an alkali metal hydroxide such as lithium hydroxide, potassium hydroxide, soidum hydroxide, cesium hydroxide, etc. However, sodium hydroxide and potassium hydroxide are preferred since they are commercially available in pellet form. The oxidation is also carried out under an inert atmosphere of a gas such as nitrogen, helium, argon, etc. and at a temperature of from about 15° C. to about 85° C. although a temperature range of 25°-75° C. is preferred. The oxidation is carried out over a period of time of from about an hour or so to about six hours or more.

The invention will be described in greater detail in conjunction with the following specific examples.

EXAMPLE 1

Preparation of 9,10-bis-(chloromethyl)anthracene

Into a solution of 100 ml. of tetrahydrothiophene-1,1-dioxide and 30ml. of concentrated aqueous hydrochloric acid was bubbled gaseous hydrogen chloride. To this solution was added 22.5 g. of anthracene and 30 ml. of formalin while the introduction of gaseous HCl was continued and as the temperature of the reaction mixture was raised to 65° C. The introduction of gaseous HCl was stopped when the solution became saturated and heating at 65° C. was continued for a total of three hours. The reaction mixture was allowed to cool overnight; 70 ml. of water was added and the precipitated product was collected by filtration and washed twice with 50 ml. portions of acetone. After drying, there was obtained 33 g. (95% yield) of 9,10-bis(chloromethyl)anthracene; m.p. 238°-243° C.

EXAMPLE 2

Preparation of 9,10-anthracenedicarboxaldehyde

To a solution of 162.2 g. of nitropropane dissolved in 900 ml. of methanol and 1400 ml. of dimethylsulfoxide under an atmosphere of argon was added 102.0 g. of pellet potassium hydroxide. After ten minutes of stirring, the KOH had dissolved and the temperature of the resulting solution had reached 37° C. To this solution was added 227.7 g. of 9,10-bis(chloromethyl)anthracene and the reaction mixture was stirred vigorously. After twenty minutes, an orange precipitate began to form and the temperature of the reaction mixture had increased to 60° C. A water bath was immediately placed under the reaction flask, bringing the temperature of the reaction mixture down to 25° C. After a total reaction time of two hours, two liters of brine was added to the reaction mixture. The resulting suspension was allowed to stand in an ice-bath for one hour and then was filtered. The weight of the wet cake so obtained was 393 g. A 200 g. portion of the wet cake was dissolved in 1600 ml. of hot toluene.

The hot toluene soluiton was filtered and allowed to cool slowly whereupon the 9,10-anthracenedicarboxaldehyde separated as orange crystals. The product was removed by filtration and dried whereupon there was obtained 43.7 g. (45% yield); m.p. 197°-215° C.

I claim:

1. The process of preparing 9,10-anthracenedicarboxaldehyde which comprises oxidizing 9,10-bis(chloromethyl)anthracene with 2-nitropropane in a binary solvent system consisting essentially of dimethylsulfoxide or dimethylformamide and an alkanol ($C_1$–$C_4$) in the presence of an alkali metal hydroxide and under an inert atmosphere at a temperature of from about 15° C. to about 85° C. for a period of time sufficient for a substanial degree of oxidation to occur.

2. The method according to claim 1 wherein the solvent system is dimethylsulfoxide and methanol and the alkali metal hydroxide is KOH.

3. The method according to claim 1 wherein the solvent system is dimethylsulfoxide and ethanol and the alkali metal hydroxide is NaOH.

4. The method according to claim 1 wherein the solvent system is dimethylformamide and methanol and the alkali metal hydroxide is KOH.

5. The method according to claim 1 wherein the solvent system is dimethylformamide and ethanol and the alkali metal hydroxide is NaOH.

* * * * *